(12) United States Patent
Tanaka et al.

(10) Patent No.: US 12,310,789 B2
(45) Date of Patent: May 27, 2025

(54) ULTRASOUND DIAGNOSTIC APPARATUS

(71) Applicant: FUJIFILM Healthcare Corporation, Kashiwa (JP)

(72) Inventors: Hiroki Tanaka, Chiba (JP); Nobuhiko Fujii, Chiba (JP); Haruka Mukawa, Chiba (JP); Takayuki Iwashita, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 108 days.

(21) Appl. No.: 18/205,633

(22) Filed: Jun. 5, 2023

(65) Prior Publication Data

US 2023/0404526 A1     Dec. 21, 2023

(30) Foreign Application Priority Data

Jun. 17, 2022 (JP) ................. 2022-097966

(51) Int. Cl.
| | |
|---|---|
| *A61B 8/14* | (2006.01) |
| *A61B 8/00* | (2006.01) |
| *G01S 7/52* | (2006.01) |
| *G01S 15/89* | (2006.01) |

(52) U.S. Cl.
CPC ............ *A61B 8/145* (2013.01); *A61B 8/4488* (2013.01); *A61B 8/54* (2013.01); *G01S 7/5209* (2013.01); *G01S 15/8925* (2013.01); *G01S 15/8995* (2013.01)

(58) Field of Classification Search
CPC ......... A61B 8/145; A61B 8/4488; A61B 8/54; A61B 8/44; A61B 8/5215; G01S 7/5209; G01S 15/8925; G01S 15/8995; G01S 7/52085; G01S 15/8927
See application file for complete search history.

(56) References Cited

U.S. PATENT DOCUMENTS

| | | | |
|---|---|---|---|
| 6,416,477 B1 | 7/2002 | Jago | |
| 2017/0252007 A1* | 9/2017 | Mine | ................. A61B 8/4218 |
| 2019/0310367 A1* | 10/2019 | Olsson | ............... G01S 7/52085 |
| 2020/0405270 A1* | 12/2020 | Ota | ......................... A61B 8/06 |

FOREIGN PATENT DOCUMENTS

| | | |
|---|---|---|
| JP | 4860945 B2 | 1/2012 |
| JP | 5921133 B2 | 5/2016 |

* cited by examiner

*Primary Examiner* — Alexei Bykhovski
(74) *Attorney, Agent, or Firm* — Paul Teng

(57) ABSTRACT

A first beam scanning plane and a second beam scanning plane are formed alternately. For formation of the first beam scanning plane, transmission/reception control is performed so that the beam deflection angle increases continuously toward the negative side from a first end to a second end in the electronic scanning direction. For formation of the second beam scanning plane, transmission/reception control is performed so that the beam deflection angle increases continuously toward the positive side from the second end to the first end in the electronic scanning direction.

8 Claims, 18 Drawing Sheets

ULTRASOUND DIAGNOSTIC APPARATUS

CROSS REFERENCE TO RELATED APPLICATION

This application claims priority to Japanese Patent Application No. 2022-097966 filed on Jun. 17, 2022, which is incorporated herein by reference in its entirety including the specification, claims, drawings, and abstract.

TECHNICAL FIELD

The present disclosure relates to an ultrasound diagnostic apparatus and, in particular, relates to a spatial compounding technique.

BACKGROUND

An ultrasound diagnostic apparatus transmits ultrasound waves to a subject and receives reflected waves from the subject, thereby forming and displaying an ultrasound image. The ultrasound image includes random acoustic noise (also referred to as speckle noise). As a technique for reducing such noise, spatial compound imaging is known.

In spatial compound imaging, for example, first frame data (hereinafter "frame data" are simply referred to as "frame") are obtained by performing first beam scanning while maintaining a beam deflection angle of $-\phi$ degrees. Subsequently, a second frame is obtained by performing second beam scanning while maintaining a beam deflection angle of 0 degrees. Subsequently, a third frame is obtained by performing third beam scanning while maintaining a beam deflection angle of $+\phi$ degrees. This sequence is performed cyclically. As a result, a frame array is obtained. The frame array consists of a first frame, a second frame, a third frame, a first frame, a second frame, a third frame, and so on, which are successive in chronological order. Three frames that are successive on a time axis are synthesized at each point of synthesis in time, thereby generating a synthesized frame.

The synthesized frame includes a plurality of portions. Specifically, the synthesized frame includes a triple overlapping portion, a double overlapping portion, and a non-overlapping portion. Among these, the triple overlapping portion and the double overlapping portion are typically displayed. It is known that spatial compound imaging produces an increased compounding effect with a greater maximum beam deflection angle difference (in the above-described example, $2\phi$). As the above-described double overlapping portion has a small beam deflection angle difference, the spatial compounding effect cannot be obtained sufficiently.

In conventional spatial compound imaging, the frame synthesis count (or beam deflection angle count) is an odd number such as 3, 5, or 7. Although spatial compound imaging apparently produces no decrease in frame rate, an increase in frame synthesis count causes a decrease in temporal responsivity.

Document 1 (JP 4860945) and Document 2 (U.S. Pat. No. 6,416,477) disclose conventional spatial compound imaging. Document 3 (JP 5921133) discloses a 1.25D probe. None of these documents discloses changing the beam deflection angle continuously during beam scanning from a first end to a second end in an electronic scanning direction.

SUMMARY

The present disclosure is directed toward implementing spatial compound imaging that can enlarge the overlapping region even if the synthesized frame count is low. Alternatively, the present disclosure is directed toward achieving good temporal responsivity and good spatial compounding effect simultaneously.

According to one aspect of the present disclosure, there is provided an ultrasound diagnostic apparatus comprising a transducer array including a plurality of transducers that are successive in an electronic scanning direction; a controller that controls operation of the transducer array to successively form a plurality of beam scanning planes including a first beam scanning plane and a second beam scanning plane; and a synthesizer that synthesizes a plurality of items of frame data that are obtained through formation of the plurality of beam scanning planes, wherein the first beam scanning plane is composed of a plurality of first beams that are successive in the electronic scanning direction, wherein the deflection angle of the plurality of first beams increases continuously toward a negative side from a first end to a second end in the electronic scanning direction, wherein the second beam scanning plane is composed of a plurality of second beams that are successive in the electronic scanning direction, and wherein the deflection angle of the plurality of second beams increases continuously toward a positive side from the second end to the first end.

BRIEF DESCRIPTION OF DRAWINGS

Embodiments of the present disclosure will be described based on the following figures, wherein.

DESCRIPTION OF EMBODIMENTS

Figure 1:
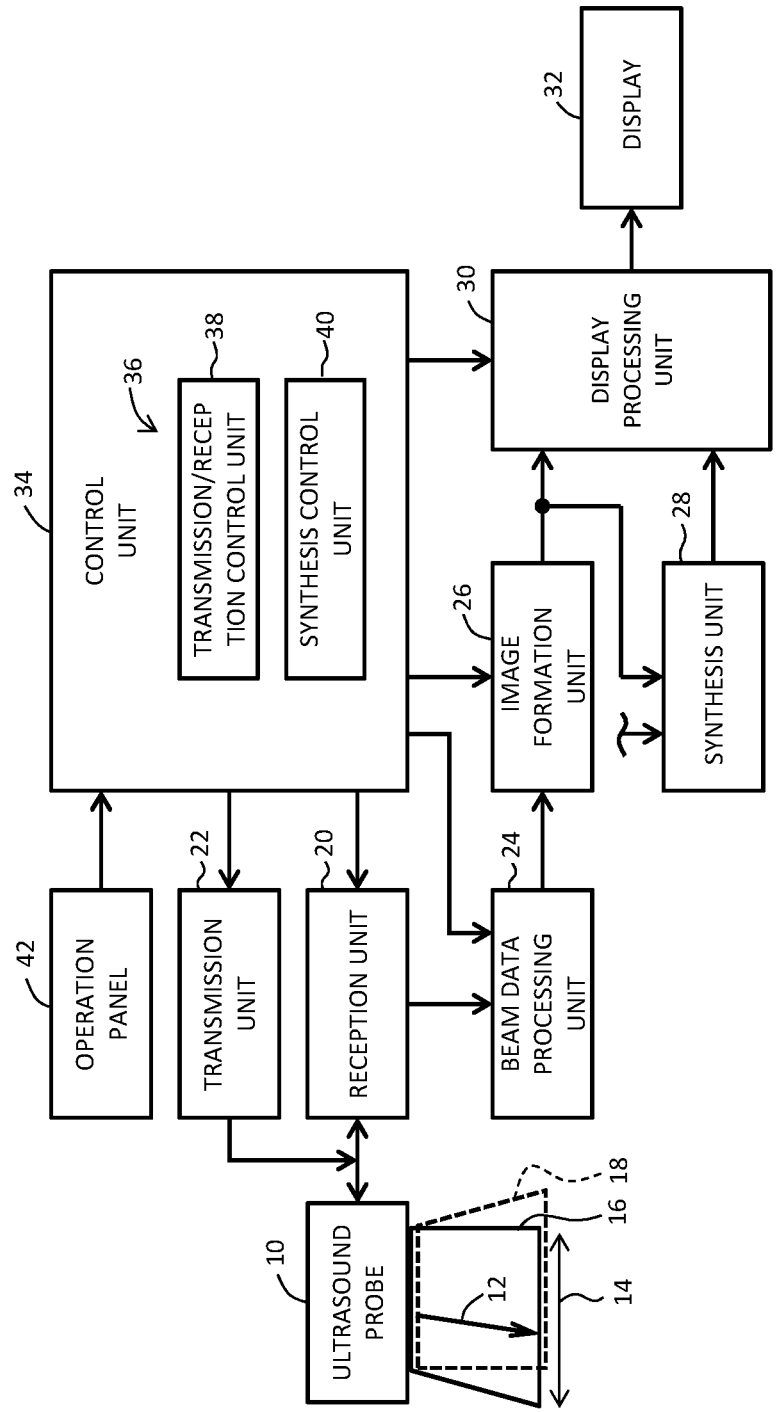
FIG. 1 illustrates an example structure of an ultrasound diagnostic apparatus according to an embodiment of the present disclosure.

Embodiments of the present disclosure will be described below with reference to the accompanying drawings.

(1) Overview of Embodiments

An ultrasound diagnostic apparatus according to an embodiment of the present disclosure includes a transducer array, a controller, and a synthesizer. The transducer array includes a plurality of transducers that are successive in an electronic scanning direction. The controller controls the operation of the transducer array to successively form a plurality of beam scanning planes including a first beam scanning plane and a second beam scanning plane. The synthesizer synthesizes a plurality of items of frame data that are obtained through the formation of the plurality of beam scanning planes. The first beam scanning plane is composed of a plurality of first beams that are successive in the electronic scanning direction. The beam deflection angle of the plurality of first beams increases continuously toward the negative side from a first end to a second end in the electronic scanning direction. The second beam scanning plane is composed of a plurality of second beams that are successive in the electronic scanning direction. The beam deflection angle of the plurality of second beams increases continuously toward the positive side from the second end to the first end in the electronic scanning direction. Examples of the controller include a control unit, a spatial compound control unit, and a transmission/reception control unit, which will be described later. An example of the synthesizer is a synthesis unit, which will be described later.

The first beam scanning plane has a first divergent shape including a deep portion that expands toward the negative electronic scanning direction, and the second beam scanning plane has a second divergent shape including a deep portion that expands toward the positive electronic scanning direction. As such, even if the synthesized frame count is low, a region where the first beam scanning plane and the second beam scanning plane overlap one another (overlapping region) can be enlarged in the electronic scanning direction. Therefore, good temporal responsivity and good spatial compounding effect are achieved simultaneously.

In an embodiment, the first divergent shape is a trapezoidal shape, which has a lower side that elongates in the negative electronic scanning direction. The second divergent shape also is a trapezoidal shape, which has a lower side that elongates in the positive electronic scanning direction. Each of the lower side of the first divergent shape and the lower side of the second divergent shape is either a straight line or a curve (arc). Similarly, each of the upper side of the first divergent shape and the upper side of the second divergent shape also is either a straight line or a curve (arc). In actual space, the two lower sides do not match each other, but the two upper sides match each other. If the first divergent shape is flipped horizontally, the horizontally flipped first divergent shape matches the second divergent shape. In other words, the first divergent shape and the second divergent shape are mutually symmetrical.

The continuous increase of the beam deflection angle includes stepwise increase of the beam deflection angle. On the first beam scanning plane, the beam deflection angle difference between adjacent beams increases gradually from the first end to the second end in the electronic scanning direction. On the second beam scanning plane, the beam deflection angle difference between adjacent beams increases gradually from the second end to the first end in the electronic scanning direction.

The controller controls the operation of a transmission unit and a reception unit, thereby controlling the operation of the transducer array indirectly. Each of the above-described beams is an acoustic ray or a scanning line. More specifically, each of the above-described beams is a transmission/reception beam when parallel reception-beam forming is not performed, and is a transmission beam when parallel reception-beam forming is performed. When parallel reception-beam forming is performed, a plurality of reception beams that fan out radially according to a beam deflection angle function may be formed simultaneously.

In an embodiment, the controller sets the deflection angle of the plurality of first beams according to a first beam deflection angle function, and sets the deflection angle of the plurality of second beams according to a second beam deflection angle function. In a coordinate system defined by a first axis that represents the position in the electronic scanning direction and a second axis that represents the beam deflection angle, the first beam deflection angle function is represented by a first line, and the second beam deflection angle function is represented by a second line. In the coordinate system, each of the first line and the second line is either a straight line or a curve. In the coordinate system, the first line and the second line are parallel with each other.

On the first beam scanning plane, the deflection angle of a first beam corresponding to the first end is 0 degrees or $+\zeta$ degrees, and the deflection angle of a first beam corresponding to the second end is $-\alpha$ degrees (where $|\alpha|>0$ or $|\alpha|>|\zeta|>0$). On the second beam scanning plane, the deflection angle of a second beam corresponding to the second end is 0 degrees or $-\zeta$ degrees, and the deflection angle of a second beam corresponding to the first end is $+\alpha$ degrees.

Each of $+\zeta$ and $-\zeta$ serves as a minus offset. Adding $+\zeta$ and $-\zeta$ enables further enlargement of the overlapping region in the electronic scanning direction. If that much enlargement is not sought, 0 may be chosen rather than $+\zeta$ and $-\zeta$.

In an embodiment, the transducer array includes a plurality of transducer rows that are successive in a lateral axis direction that is perpendicular to a longitudinal axis direction serving as the electronic scanning direction. Each of the transducer rows is composed of a plurality of transducers that are successive in the electronic scanning direction. The plurality of beam scanning planes include the first beam scanning plane, the second beam scanning plane, a third beam scanning plane, and a fourth beam scanning plane. The third beam scanning plane is composed of a plurality of third beams that are successive in the electronic scanning direction. The beam deflection angle of the plurality of third beams increases continuously toward the negative side from the first end to the second end in the electronic scanning direction. The fourth beam scanning plane is composed of a plurality of fourth beams that are successive in the electronic scanning direction. The beam deflection angle of the plurality of fourth beams increases continuously toward the positive side from the second end to the first end in the electronic scanning direction. To form the first beam scanning plane and the second beam scanning plane, a first acoustic aperture size is set in the lateral axis direction in the transducer array. To form the third beam scanning plane and the fourth beam scanning plane, a second acoustic aperture size is set in the lateral axis direction in the transducer array.

The first acoustic aperture size and the second acoustic aperture size are different from each other.

The above-described structure combines combination of beam deflection angle variations and switching of aperture sizes in the lateral axis direction. The above-described structure is implemented using, for example, a 1.25D probe, a 1.5D probe, a 1.75D probe, or a 2D probe. The beam scanning planes may be formed in any predetermined order. For example, a series of beam scanning planes may be formed in the following order: the first beam scanning plane, the second beam scanning plane, the third beam scanning plane, and the fourth beam scanning plane, or a series of beam scanning planes may be formed in the following order: the first beam scanning plane, the third beam scanning plane, the second beam scanning plane, and the fourth beam scanning plane.

An ultrasound diagnostic apparatus according to an embodiment of the present disclosure includes a filter that is applied to a plurality of first reception signals corresponding to the plurality of first beams and a plurality of second reception signals corresponding to the plurality of second beams. The control unit varies characteristics of the filter in accordance with the deflection angle of the plurality of first beams and the deflection angle of the plurality of second beams. Ultrasound propagation distance varies in accordance with beam deflection angle. In other words, characteristics of the reception signals vary in accordance with beam deflection angle. The above-described structure therefore varies characteristics of the filter in accordance with variation of characteristics of the reception signals.

In an embodiment, the count of the plurality of beam scanning planes is an even number. The count is, for example, 2 or 4. A beam scanning plane set consisting of an even number of beam scanning planes is formed cyclically. In an embodiment, scanning performed at a fixed beam deflection angle of 0 degrees (conventional intermediate scanning) is unnecessary.

(2) Details of Embodiments

FIG. 1 illustrates an ultrasound diagnostic apparatus according to an embodiment of the present disclosure. This ultrasound diagnostic apparatus is a medical apparatus installed in, for example, a healthcare facility and is used for performing ultrasound inspection on a subject. Control and processing according to each of embodiments of the present disclosure, which will be described later, are performed using the structure illustrated in FIG. 1.

An ultrasound probe 10 includes a transducer array composed of a plurality of transducers that are aligned in a linear arrangement. The transducer array forms an ultrasound beam 12. Repeated electronic scanning of the ultrasound beam 12 forms beam scanning planes (two-dimensional data capture regions) successively. In an embodiment, according to spatial compound imaging, a plurality of types of beam scanning planes are formed cyclically. In some embodiments described later, a first beam scanning plane 16 and a second beam scanning plane 18 are formed alternately. In that case, the synthesized frame count is 2.

A transmission unit 22 is an electronic circuit that serves as a transmission beam former. During transmission, the transmission unit 22 supplies a plurality of transmission signals to the transducer array in parallel. As a result, ultrasound waves are emitted to a living body. That is, a transmission beam is formed.

A reception unit 20 is an electronic circuit that serves as a reception beam former. During reception, reflected waves from the living body are received by the transducer array, and then a plurality of reception signals are output from the transducer array to the reception unit 20 in parallel. The reception unit 20 applies phase alignment and summing to the plurality of reception signals, thereby generating reception beam data.

In response to a single electronic scan, one reception frame (set of reception frame data) is formed. One reception frame is composed of a plurality of items of reception beam data that are successive in the electronic scanning direction. Each item of beam data is composed of a plurality of items of echo data that are successive in a depth direction. In the illustrated example structure, a first reception frame corresponding to the first beam scanning plane and a second reception frame corresponding to the second beam scanning plane are obtained alternately.

A beam data processing unit 24 includes an envelope detection circuit, a filter, a log compression circuit, and others. The filter is, for example, a band-pass filter (BPF). Characteristics of the band-pass filter are changed dynamically in accordance with depth of the point of reception. In an embodiment, characteristics of the band-pass filter are further changed in accordance with beam deflection angle. This will be described in detail later.

An image formation unit 26 is a circuit that generates a plurality of display frames from a plurality of reception frames. Specifically, the image formation unit 26 is composed of a digital scan converter (DSC) that has a coordinate conversion function, a pixel interpolation function, a frame rate change function, and other functions. An individual display frame corresponds to a tomographic image that is in the form of a still-frame image. An image other than a tomographic image may be formed as an ultrasound image. During implementation of spatial compound imaging, a plurality of display frames which are formed are transmitted to a synthesis unit 28.

The synthesis unit 28 serves as the synthesizer. The synthesis unit 28 successively retrieves, from display frame arrays which are input, display frame pairs each consisting of two temporally adjacent display frames, and synthesizes these for each display frame pair to generate a synthesized frame. A synthesized frame array is output from the synthesis unit 28. For synthesis of a display frame pair, for example, a rectangular overlapping portion is extracted, and two non-overlapping portions (two ends) are discarded.

It should be noted that the synthesized frame array may be generated by synthesizing frame arrays that have not been subjected to coordinate conversion. The synthesized frame array may be generated by synthesizing RF frame arrays that have not been subjected to envelope detection.

A display processing unit 30 has a graphic synthesis function, a color calculation function, and other functions. The synthesized frame array is transmitted from the display processing unit 30 to a display 32. The display 32 displays the synthesized frame array in the form of a tomographic image (video image). The display 32 is composed of an organic EL display device, an LCD, or the like. The synthesis unit 28 and the display processing unit 30 described above are each composed of a processor. A control unit 34, which will be described below, may serve as the synthesis unit 28 and the display processing unit 30.

The control unit 34 serves as the controller. Specifically, the control unit 34 is composed of a CPU that executes a program. The control unit 34 controls the operation of components illustrated in FIG. 1 and performs various types of information processing. Specifically, the control unit 34 serves as a transmission/reception control unit 38. Further, the control unit 34 serves as a spatial compound control unit 36. For spatial compound control, the transmission/reception control unit 38 and a synthesis control unit 40 function. Specific details of the spatial compound control will be described later. An operation panel 42 connected to the control unit 34 is an input device that includes a plurality of switches, a plurality of knobs, a keyboard, a trackball, and other controls.

Figure 2:
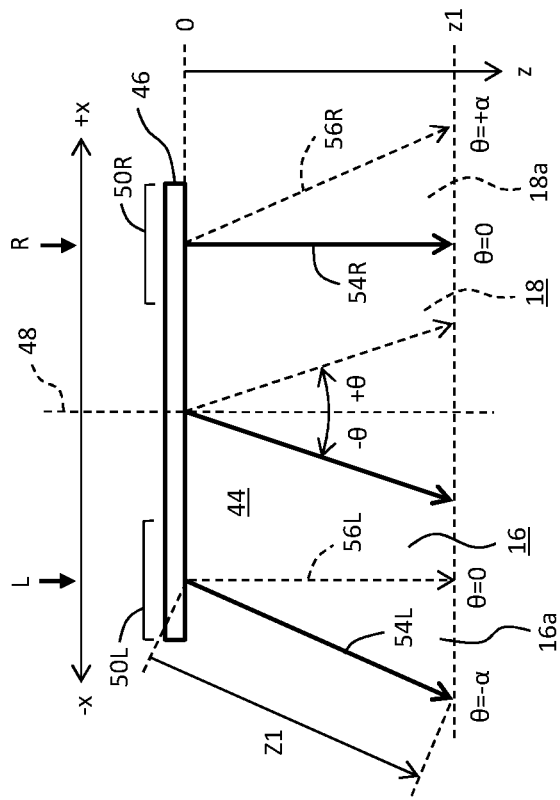
FIG. 2 illustrates beam scanning according to a first embodiment of the present disclosure.

FIG. 2 illustrates beam scanning according to a first embodiment of the present disclosure. The x axis, which is a horizontal axis, represents the position in the electronic scanning direction. The positive electronic scanning direction is denoted as +x, and the negative electronic scanning direction is denoted as −x. A transducer array 46 is composed of a plurality of transducers that are successive along the x axis. The z axis, which is perpendicular to the x axis, is a depth axis. A transmission/reception aperture is set for the transducer array 46, and the transmission/reception aperture is electronically scanned.

In FIG. 2, reference numeral 48 represents a center line that runs through the center of the transducer array 46. A beam deflection angle is denoted as θ. For the beam deflection angle θ, the counterclockwise direction represents the positive side (+θside), and the clockwise direction represents the negative side (−θ side). R represents a first end in the electronic scanning direction, and L represents a second end in the electronic scanning direction. A transmission/reception aperture 50R is an aperture corresponding to the first end R. A transmission/reception aperture 50L is an aperture corresponding to the second end L. In the illustrated example, the center position of the transmission/reception aperture 50R coincides with the position of the first end R, and the center position of the transmission/reception aperture 50L coincides with the position of the second end L. It should be noted that the transmission/reception aperture may be set to either extend partially beyond the transducer array 46 or extend across an actual end of the transducer array 46. In such cases, the transmission/reception aperture is composed of an actual aperture portion and a virtual aperture portion.

The electronic scanning of an ultrasound beam is oriented either in the +x direction or in the −x direction. In other words, the transmission/reception aperture is electronically scanned in the +x direction or in the −x direction. The ultrasound beam is, for example, a transmission beam and a reception beam. The ultrasound beam may be understood as being a transmission/reception total beam. When parallel reception-beam forming is performed, a plurality of reception beams are formed simultaneously in response to a single transmission. In such cases, an arrangement of a plurality of reception beams may be determined according to a beam deflection angle function, which will be described later. In the following description, an ultrasound beam is simply referred to as a beam. It should be noted that z1 represents a maximum depth (depth range) over which imaging is performed.

In the first embodiment, the first beam scanning plane 16 and the second beam scanning plane 18 are formed alternately. More specifically, the first beam scanning plane 16 is composed of a plurality of first beams that are successive in the electronic scanning direction. Specifically, it is composed of n beams including a first beam 54R corresponding to the first end R to a first beam 54L corresponding to the second end L. The beam deflection angle θ of the plurality of first beams increases continuously toward the negative side (−θ side) from the first beam 54R to the first beam 54L.

In the first embodiment, the beam deflection angle θ of the first beam 54R is 0 degrees, and the beam deflection angle of the first beam 54L is −α. With attention focused on the deep portion of the first beam scanning plane 16, the beam-to-beam pitch increases continuously from the first beam 54R to the first beam 54L.

The second beam scanning plane 18 is composed of a plurality of second beams that are successive in the electronic scanning direction. Specifically, it is composed of n beams including a second beam 56L corresponding to the second end L to a second beam 56R corresponding to the first end R. The beam deflection angle θ of the plurality of second beams increases continuously toward the positive side (+θ side) from the second beam 56L to the second beam 56R.

In the first embodiment, the beam deflection angle θ of the second beam 56L is 0 degrees, and the beam deflection angle of the second beam 56R is +α. With attention focused on the deep portion of the second beam scanning plane 18, the beam-to-beam pitch increases continuously from the second beam 56L to the second beam 56R.

For formation of the first beam scanning plane 16, non-parallel scan to the −x direction is performed. For formation of the second beam scanning plane 18, non-parallel scan to the +x direction is performed.

The first beam scanning plane 16 has a first divergent shape. The second beam scanning plane 18 has a second divergent shape. The first divergent shape is a trapezoid with a right angle, with only its lower side extending in the negative electronic scanning direction. The second divergent shape is also a trapezoid with a right angle, with only its lower side extending in the positive electronic scanning direction.

Reference numeral 44 represents an overlapping region between the first beam scanning plane 16 and the second beam scanning plane 18. The overlapping region 44 is rectangular. The overlapping region 44 constitutes a display region. A triangular end region 16a which belongs only to the first beam scanning plane 16 is present on the negative side (−x side) of the overlapping region 44. A triangular end region 18a which belongs only to the second beam scanning plane 18 is present on the positive side (+x side) of the overlapping region 44. The two end regions 16a and 18a are portions that are not imaged.

In the first embodiment, |α|>0 holds, and specifically, |α| is set in a range of, for example, 10 to 20 degrees. It may be set in a range of 20 to 30 degrees or may be set in a range of 5 to 10 degrees. It should be noted that Z1 represents ultrasound propagation distance corresponding to the depth z1 when the beam deflection angle θ is −α. To dynamically vary characteristics of the filter, ultrasound propagation distance is taken into consideration for each point of reception on the beams. In that case, round-trip propagation distance may be taken into consideration.

Figure 3:
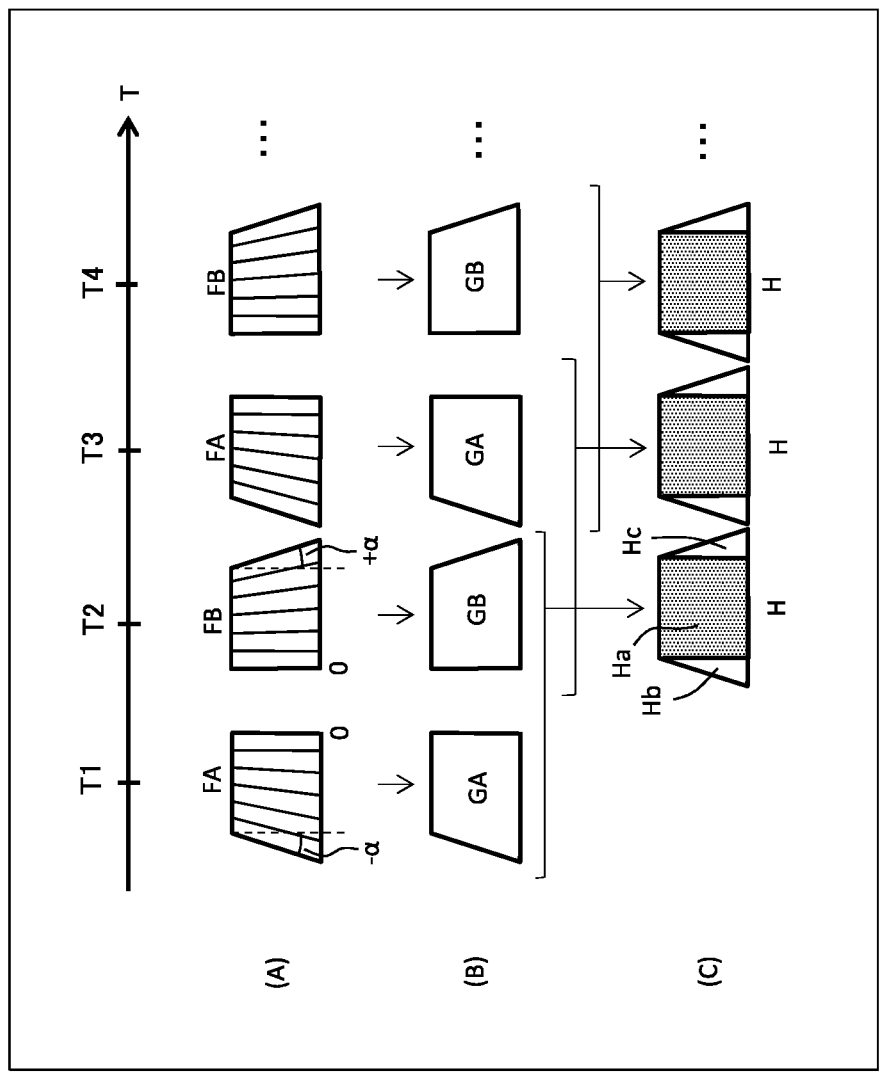
FIG. 3 illustrates a spatial compounding technique according to the first embodiment of the present disclosure.

FIG. 3 illustrates a spatial compounding technique according to the first embodiment of the present disclosure. T represents a time axis, and each of T1, T2, T3, and T4 represents a frame processing point in time. (A) illustrates a beam scanning plane array, (B) illustrates a frame array, and (C) illustrates a synthesized frame array.

The beam scanning plane array is composed of a first beam scanning plane FA, a second beam scanning plane FB, a first beam scanning plane FA, a second beam scanning plane FB, and so on. The maximum beam deflection angle θ of the first beam scanning planes FA is −α, and the maximum beam deflection angle θ of the second beam scanning planes FB is +α. As the beam scanning plane array is formed, the frame array is generated. The frame array is composed of a first frame GA, a second frame GB, a first frame GA, a second frame GB, and so on.

Synthesis processing is applied to each frame pair in the frame array to generate a synthesized frame H. Each of synthesized frames H consists of an overlapping portion Ha and non-overlapping portions Hb and Hc. The non-overlapping portions Hb and Hc are typically discarded. The overlapping portion Ha is to be imaged.

Figure 4:
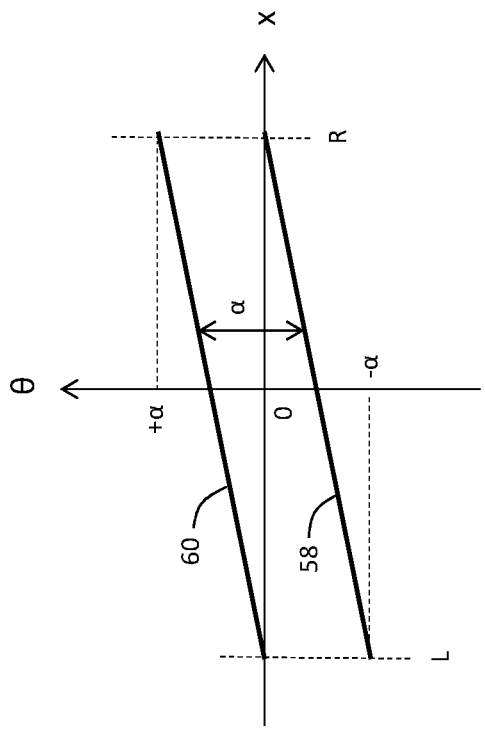
FIG. 4 illustrates a beam deflection angle function according to the first embodiment of the present disclosure.

FIG. 4 illustrates a first beam deflection angle function 58 and a second beam deflection angle function 60 according to the first embodiment of the present disclosure. The horizontal axis is the x axis, and the vertical axis represents beam deflection angle θ. For formation of the first beam scanning plane, the beam deflection angles of the first beams are set according to the first beam deflection angle function 58. For formation of the first beam scanning plane, the minimum beam deflection angle θ is 0 degrees, and the maximum beam deflection angle θ is −α degrees.

For formation of the second beam scanning plane, the beam deflection angles of the second beams are set according to the second beam deflection angle function 60. For formation of the second beam scanning plane, the minimum beam deflection angle θ is 0 degrees, and the maximum beam deflection angle θ is +α degrees. The first beam deflection angle function 58 and the second beam deflection angle function 60 are each a straight line, which are parallel each other. They are apart from each other by an interval of α.

Figure 5:
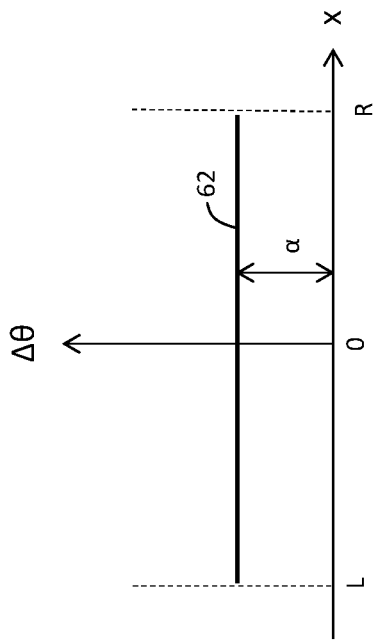
FIG. 5 illustrates a beam deflection angle difference function according to the first embodiment of the present disclosure.

FIG. 5 illustrates a beam deflection angle difference function 62 according to the first embodiment of the present disclosure. The horizontal axis is the x axis, and the vertical axis represents beam deflection angle difference Δθ. The beam deflection angle difference Δθ is always at a constant value α regardless of the position in the x-axis direction.

Figure 6:
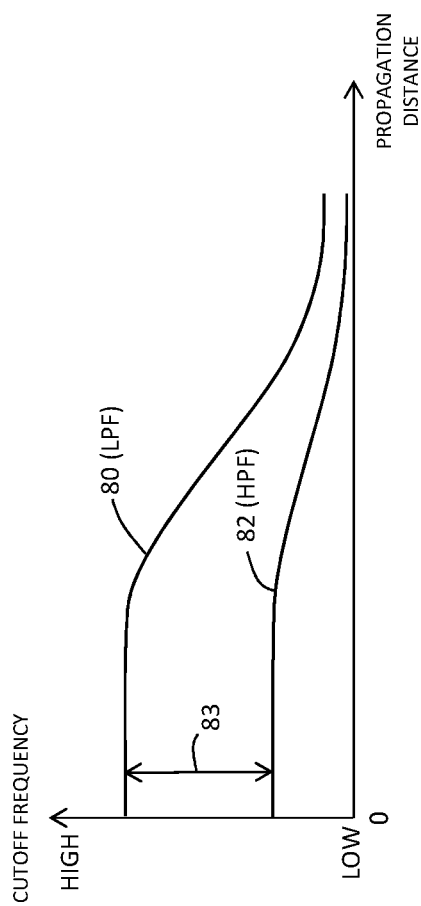
FIG. 6 illustrates characteristics of a band-pass filter.

FIG. 6 illustrates the operation of the BPF included in the beam data processing unit. The horizontal axis represents ultrasound propagation distance, and the vertical axis represents cutoff frequency. The BPF is composed of an LPF and an HPF. Reference numeral 80 represents a cutoff frequency characteristic of the LPF, and reference numeral 82 represents a cutoff frequency characteristic of the HPF. A gap 83 between the two cutoff frequency characteristics 80 and 82 corresponds to a passband. Referring to the cutoff frequency characteristics 80 and 82, as the ultrasound propagation distance increases, the cutoff frequencies of the LPF and the HPF are reduced to the lower side. The ultrasound propagation distance increases in response to increase in depth of the point of reception and increases in response to increase in beam deflection angle (increase in |θ|).

Figure 7:
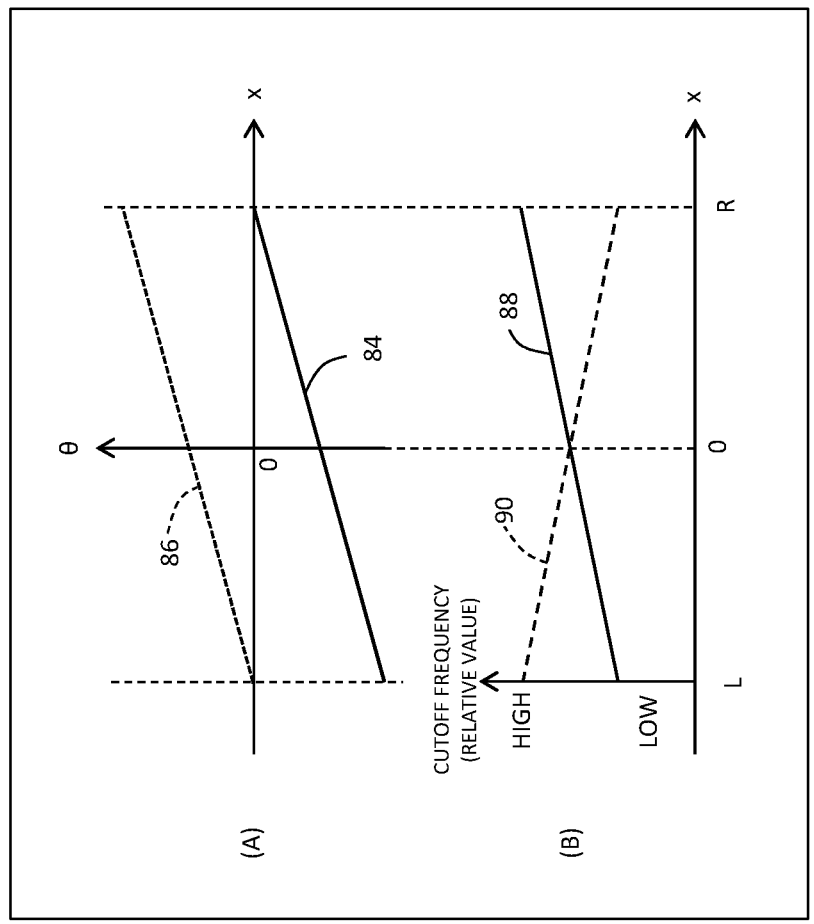
FIG. 7 illustrates changes in cutoff frequency that follow changes in beam deflection angle.

FIG. 7 illustrates control of the BPF according to an embodiment of the present disclosure. During electronic scanning of first beams, the beam deflection angle is changed according to a beam deflection angle function 84. Even if the point of reception is at the same depth, the ultrasound propagation distance increases in response to increase in beam deflection angle. With attention focused on a point of reception at a certain depth, as shown by a function 88, the cutoff frequencies of the LPF and the HPF are reduced in response to increase in beam deflection angle.

During electronic scanning of second beams, the beam deflection angle is changed according to a beam deflection angle function 86. Even if the point of reception is at the same depth, the ultrasound propagation distance increases in response to increase in beam deflection angle. With attention focused on a point of reception at a certain depth, as shown by a function 90, the cutoff frequencies of the LPF and the HPF are reduced in response to increase in beam deflection angle. It should be noted that in FIG. 7, the function 88 and the function 90 are both schematic representations. These may be curves.

Figure 8:
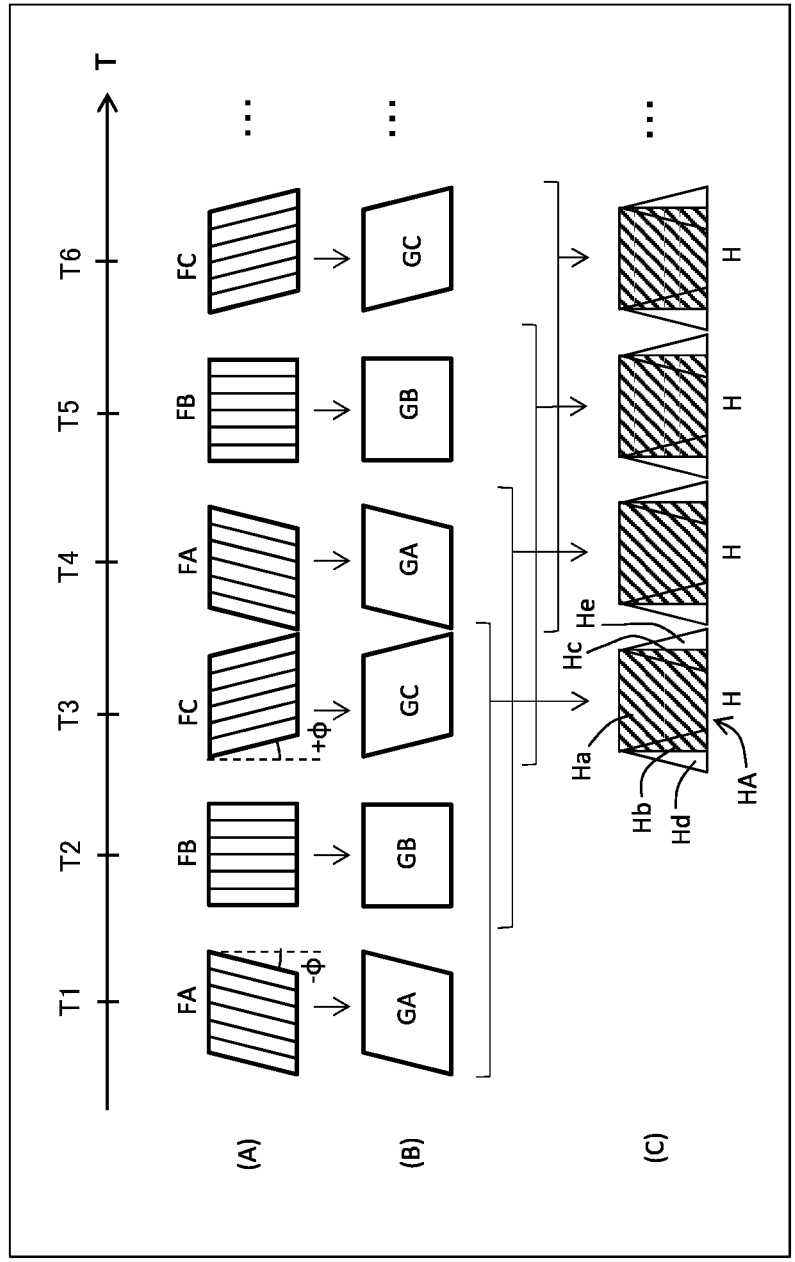
FIG. 8 illustrates a first comparative example.

FIG. 8 illustrates a first comparative example. (A) illustrates a beam scanning plane array. (B) illustrates a frame array. (C) illustrates a synthesized frame array. The beam scanning plane array includes a first beam scanning plane FA, a second beam scanning plane FB, and a third beam scanning plane FC. The first beam scanning plane FA is composed of a plurality of first beams, and their beam deflection angle is constant (−ϕ degrees). The second beam scanning plane FB is composed of a plurality of second beams, and their beam deflection angle is constant (0 degrees). The third beam scanning plane FC is composed of a plurality of third beams, and their beam deflection angle is constant (+ϕ degrees). Three frames that are successive on the time axis are synthesized, thereby generating a synthesized frame H.

The synthesized frame H consists of a triple overlapping portion Ha, double overlapping portions Hb and Hc, and non-overlapping portions Hd and He. An imaging region HA, which is hatched, is a rectangular region, and includes the triple overlapping portion Ha and the double overlapping portions Hb and Hc. In the imaging region HA, the double overlapping portions Hb and Hc have a smaller beam deflection angle difference (and fewer overlaps) than the triple overlapping portion Ha, resulting in a reduction in spatial compounding effect. Further, as the synthesized frame is generated from three frames, a temporal responsivity issue may arise in some cases.

Figure 9:
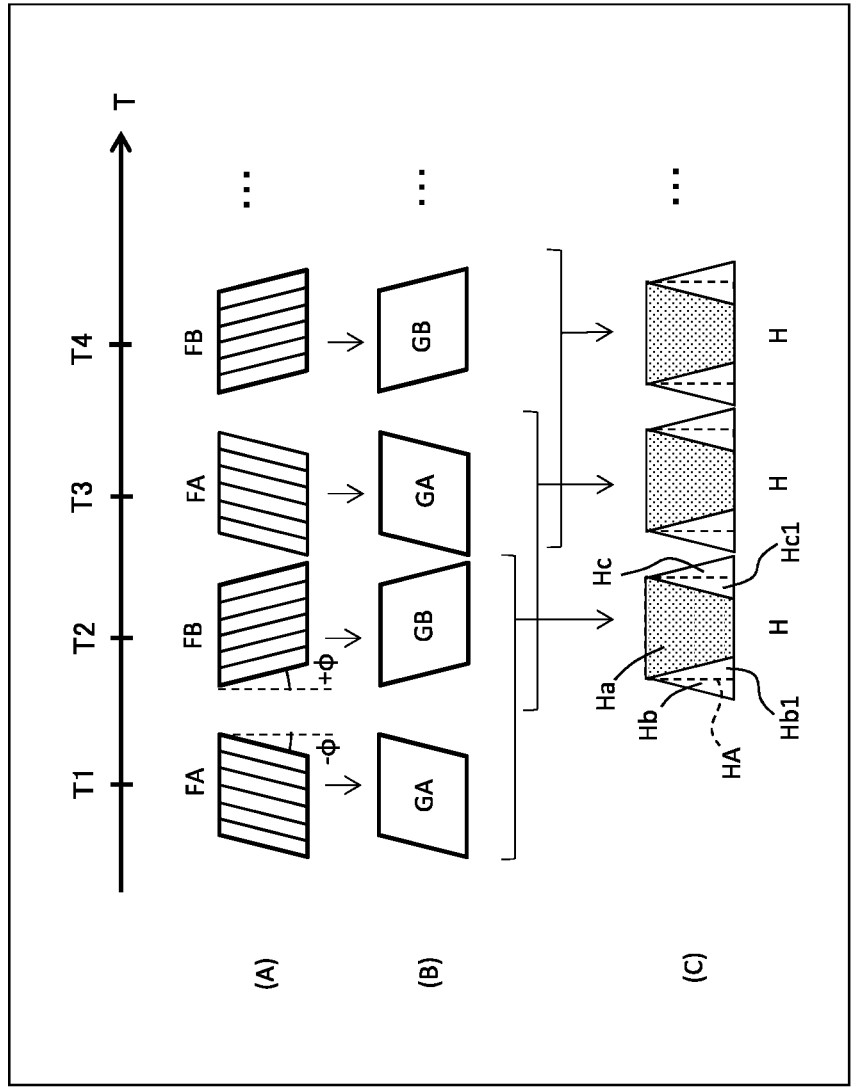
FIG. 9 illustrates a second comparative example.

FIG. 9 illustrates a second comparative example. (A) illustrates a beam scanning plane array. (B) illustrates a frame array. (C) illustrates a synthesized frame array. The beam scanning plane array includes a first beam scanning plane FA and a second beam scanning plane FB. Each of synthesized frames consists of an overlapping portion Ha and non-overlapping portions Hb and Hc. An imaging region HA, which is denoted by a broken line, is a rectangular region, and it includes a double overlapping portion Ha and non-overlapping portions Hb1 and Hc1. According to the second comparative example, in comparison with the first comparative example, although good temporal responsivity is obtained, the overall imaging region HA cannot be an overlapping region.

In contrast, according to the above-described first embodiment, a synthesized frame can be generated by two frames, and the overall rectangular imaging region in the synthesized frame can be an overlapping region. Additionally, because a relatively large beam deflection angle difference can be provided over the overall imaging region, good spatial compounding effect is obtained over the entire imaging region.

Figure 10:
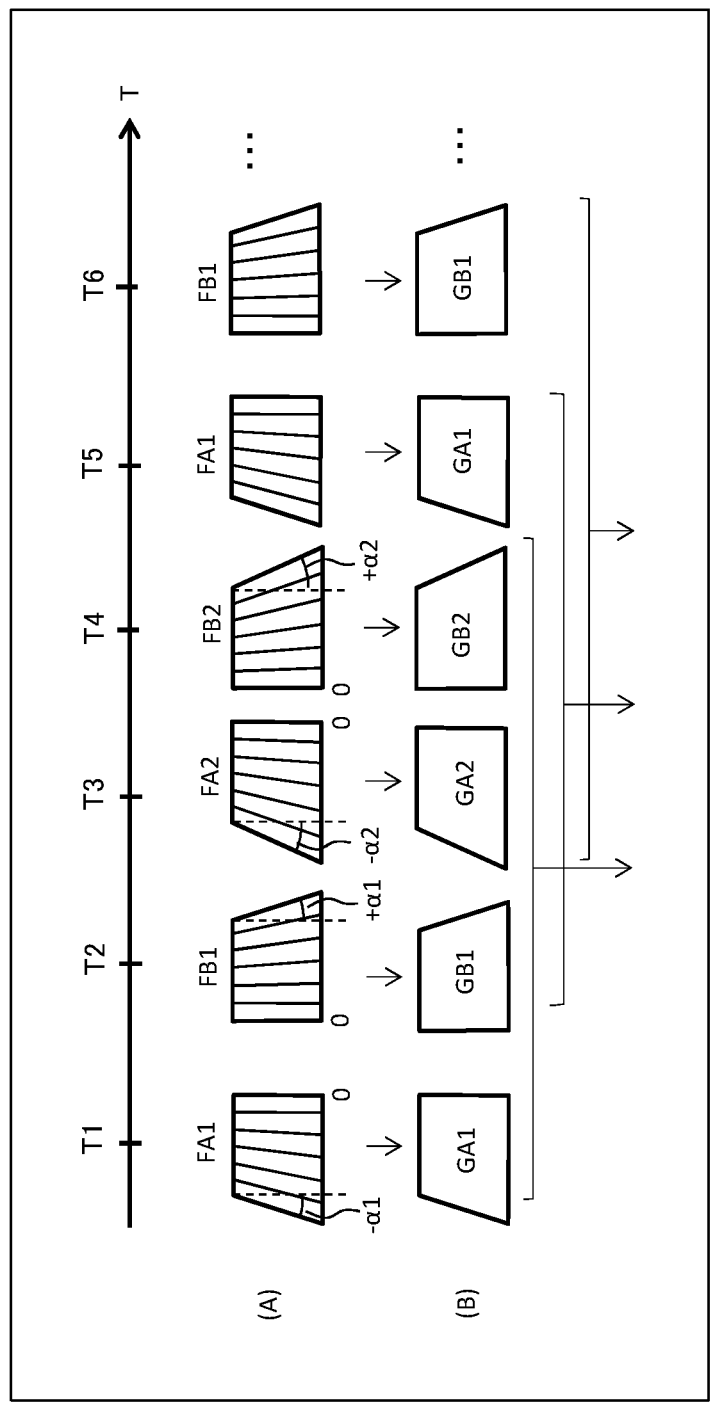
FIG. 10 illustrates a first modification of the first embodiment of the present disclosure.

FIG. 10 illustrates a first modification of the first embodiment. The beam scanning plane array includes four beam scanning planes FA1, FB1, FA2, and FB2. For formation of the beam scanning plane FA1, the beam deflection angle is increased continuously from the first end to the second end in the electronic scanning direction toward the negative side from 0 to −α1. For formation of the beam scanning plane FB1, the beam deflection angle is increased continuously from the second end to the first end in the electronic scanning direction from 0 to +α1. For formation of the beam scanning plane FA2, the beam deflection angle is increased continuously from the first end to the second end in the electronic scanning direction from 0 to −α2. For formation of the beam scanning plane FB2, the beam deflection angle is increased continuously from the second end to the first end in the electronic scanning direction from 0 to +α2. Note that in the above, |α1|<|α2| holds.

A frame array includes four frames GA1, GB1, GA2, and GB2 corresponding to the four beam scanning planes FA1, FB1, FA2, and FB2, respectively. For generation of a synthesized frame, four temporally successive frames are synthesized. For example, the frames GA1, GB1, GA2, and GB2 are synthesized. It should be noted that the four beam scanning planes FA1, FB1, FA2, and FB2 may be formed in any predetermined order.

According to the above-described first modification, as high spatial compounding effect is obtained over the entire display region, the image quality may be further improved. When higher priority is given to the time responsivity, the synthesis count may be set to 2; that is, the sequence illustrated in FIG. 3 may be employed. On the other hand, when higher priority is given to the image quality, the synthesis count may be set to 4; that is, the sequence illustrated in FIG. 10 may be employed.

Figure 11:
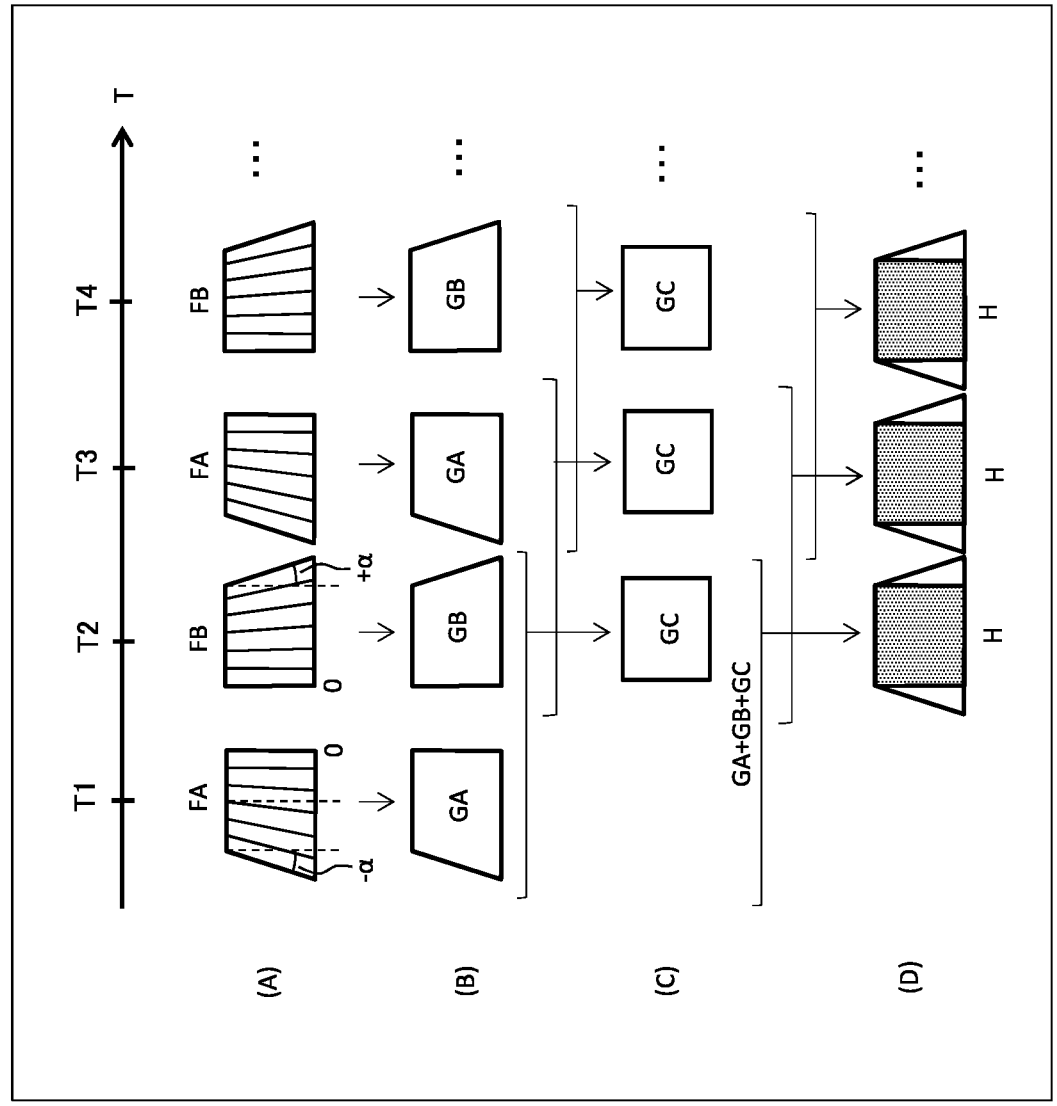
FIG. 11 illustrates a second modification of the first embodiment of the present disclosure.

FIG. 11 illustrates a second modification of the first embodiment. (A) illustrates a beam scanning plane array. (B) illustrates a frame array. (C) illustrates an intermediate synthesized frame array. (D) illustrates a synthesized frame array.

The intermediate synthesized frame array is composed of a plurality of intermediate synthesized frames GC that are generated based on the frame array. Each of the intermediate synthesized frames GC is generated for each frame pair (GA-GB pair or GB-GA pair) in the frame array by applying non-linear processing to the frame pair. The intermediate synthesized frames GC may be generated by, for example, Lagrange interpolation processing, spline interpolation processing, or other processing. The intermediate synthesized frames GC may be generated by a neural network (machine-learnt image generation model).

A synthesized frame H is generated by synthesizing three frames consisting of two frames that constitute a frame pair, and an intermediate synthesized frame that is generated from the frame pair. The synthesized frame H is generated by, for example, summing a frame GA, a frame GB, and an intermediate synthesized frame GC. According to the second modification, a higher spatial compounding effect is obtained.

Next, a second embodiment of the present disclosure will be described below by reference to FIGS. 12 to 14.

Figure 12:
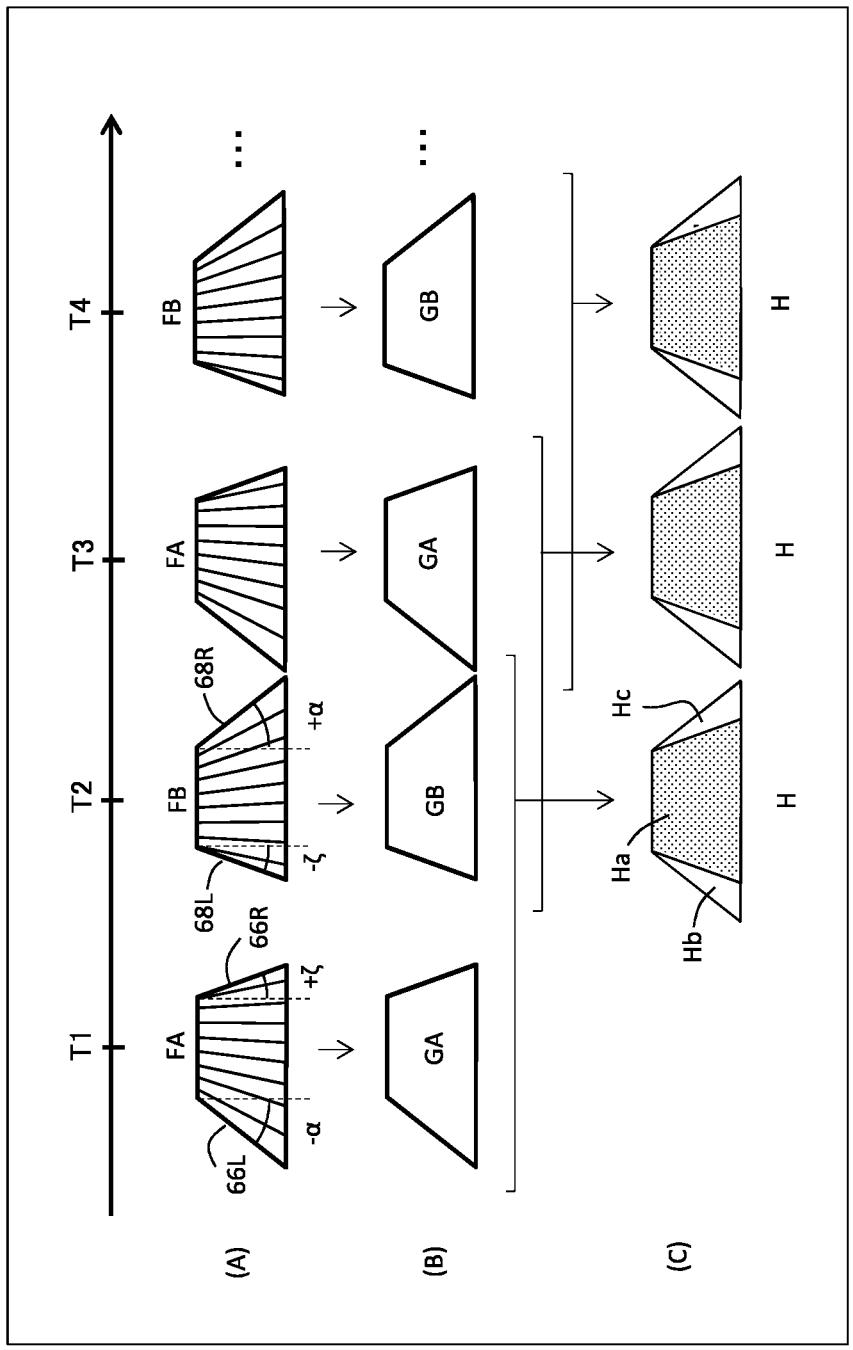
FIG. 12 illustrates a spatial compounding technique according to a second embodiment of the present disclosure.

In FIG. 12, (A) illustrates a beam scanning plane array. (B) illustrates a frame array. (C) illustrates a synthesized frame array. The beam scanning plane array consists of a plurality of first beam scanning planes FA and a plurality of second beam scanning planes FB that are formed alternately. On each of the first beam scanning planes FA, the deflection angle of a beam 66R corresponding to the first end in the electronic scanning direction is +ζ, and the deflection angle of a beam 66L corresponding to the second end in the electronic scanning direction is −α. The beam deflection angle is increased toward the negative side (−θ side) from the first end to the second end in the electronic scanning direction. Note that in the above, |α|>0 and |ζ|>0 hold.

On each of the second beam scanning planes FB, the deflection angle of a beam 68L corresponding to the second end in the electronic scanning direction is −ζ, and the deflection angle of a beam 68R corresponding to the first end in the electronic scanning direction is +α. The beam deflection angle is increased toward the positive side (+θ side) from the second end to the first end in the electronic scanning direction. Each of synthesized frames H is composed of an overlapping portion Ha and non-overlapping portions Hb and Hc. The overlapping portion Ha has a bilaterally symmetrical divergent shape. A relationship |α|>|ζ|>0 holds. It should be noted that α in the second embodiment corresponds to an angle obtained by adding ζ to α (see FIG. 2) in the first embodiment.

Figure 13:
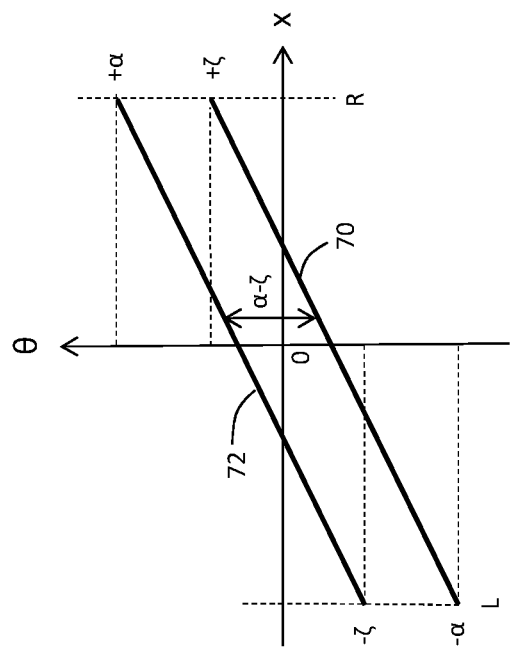
FIG. 13 illustrates a beam deflection angle function according to the second embodiment of the present disclosure.

FIG. 13 illustrates a first beam deflection angle function 70 and a second beam deflection angle function 72 according to the second embodiment of the present disclosure. For formation of the first beam scanning plane, the beam deflection angles of the first beams are set according to the first beam deflection angle function 70. For formation of the first beam scanning plane, the beam deflection angle θ at the first end is +ζ, and the beam deflection angle θ at the second end is −α.

For formation of the second beam scanning plane, the beam deflection angles of the second beams are set according to the second beam deflection angle function 72. For formation of the second beam scanning plane, the beam deflection angle θ at the second end is −ζ, and the beam deflection angle θ at the first end is +α degrees. The first beam deflection angle function 70 and the second beam deflection angle function 72 are each a straight line, and are parallel with each other. They are apart from each other by an interval of (α−ζ).

Figure 14:
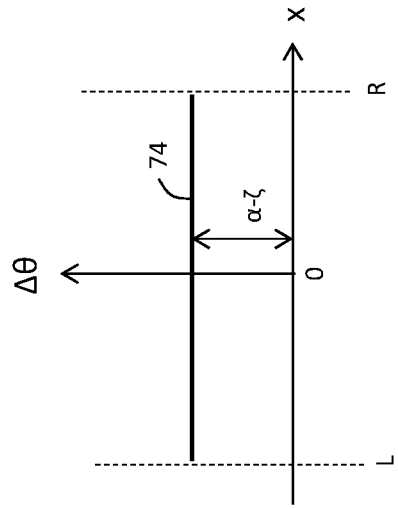
FIG. 14 illustrates a beam deflection angle difference function according to the second embodiment of the present disclosure.

FIG. 14 illustrates a beam deflection angle difference function 74 according to the second embodiment of the present disclosure. The beam deflection angle difference is always (α−ζ) regardless of the position in the x-axis direction.

As with the first embodiment, the second embodiment provides good temporal responsivity and good spatial compounding effect. Additionally, the overlapping region; that is, the imaging region, can be further enlarged.

Figure 15:
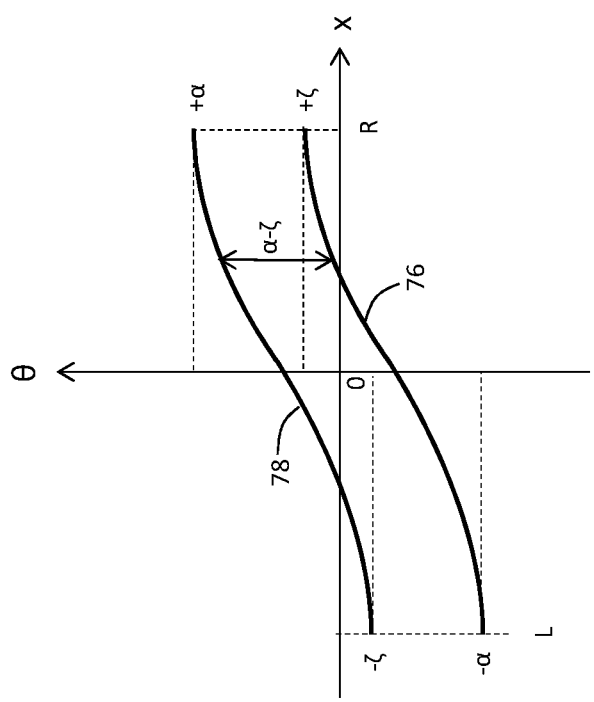
FIG. 15 illustrates a modification of the second embodiment of the present disclosure.

FIG. 15 illustrates a modification of the second embodiment of the present disclosure. For formation of the first beam scanning plane, the beam deflection angles of the first beams are set according to a first beam deflection angle function 76. For formation of the first beam scanning plane, the beam deflection angle θ at the first end is +ζ, and the beam deflection angle θ at the second end is −α. The first beam deflection angle function 76 is a curve and specifically has a shape like a logistic curve.

For formation of the second beam scanning plane, the beam deflection angles of the second beams are set according to a second beam deflection angle function 78. For formation of the second beam scanning plane, the beam deflection angle θ at the second end is −ζ, and the beam deflection angle θ at the first end is +α. The second beam deflection angle function 78 is a curve and, as with the first beam deflection angle function 76, specifically has a shape like a logistic curve. In the first embodiment, the two beam deflection angle functions illustrated in FIG. 4 may be curves.

Next, a third embodiment of the present disclosure will be described below by reference to FIGS. 16 to 18. In the third embodiment, a 1.25D probe is used as the ultrasound probe. Instead, a 1.5D probe, a 1.75D probe, or a 2D probe may be used.

Figure 16:
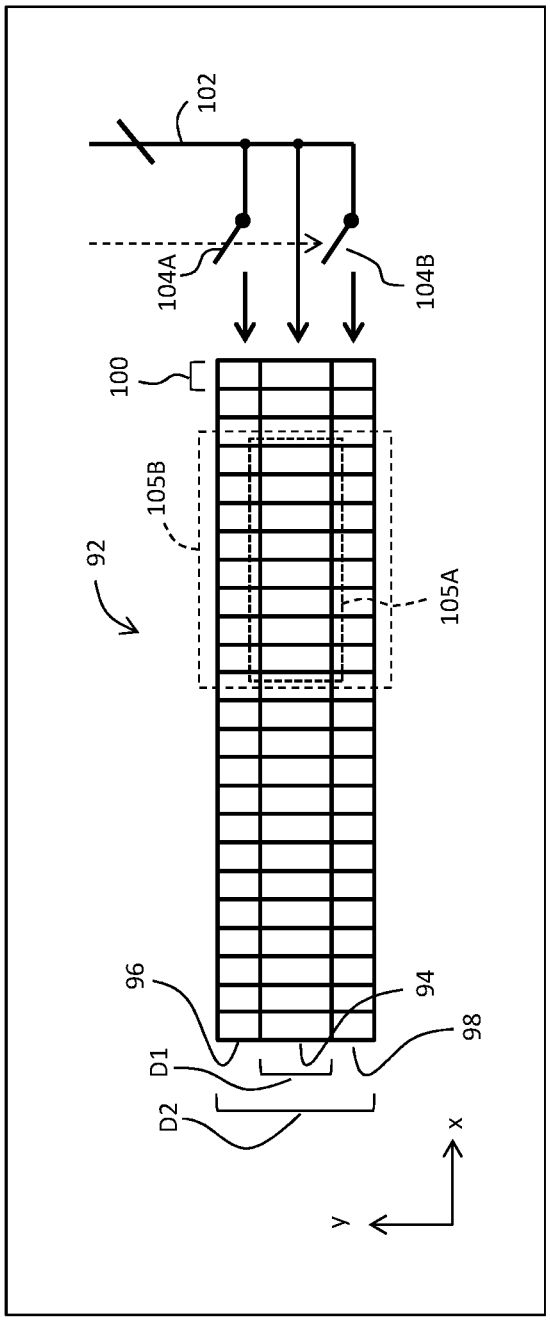
FIG. 16 illustrates a 1.25D probe according to a third embodiment of the present disclosure.

FIG. 16 illustrates a transducer array 92 disposed in the 1.25D probe. The x direction is a longitudinal axis direction serving as the electronic scanning direction, and the y direction is a lateral axis direction. The transducer array 92 is composed of three transducer rows 94, 96, and 98 that are successive in the y direction. The transducer row 94, which is located in the center, is composed of a plurality of transducers that are successive in the x direction. Similarly, the transducer row 96, which is located on one side in the y direction, and the transducer row that is located on the other side in the y direction also are each composed of a plurality of transducers that are successive in the x direction. If viewed differently, the transducer array 92 is composed of a plurality of transducer sets 100 that are successive in the x direction. Each of the transducer sets 100 is composed of three transducers that are successive in the y direction.

A signal line group 102 is composed of a plurality of signal lines connected to the plurality of transducer sets 100. When switches 104A and 104B are in the off state, the signal line group 102 is connected only to the transducer row 94. In that case, a small aperture size D1 is set in the y direction. For example, a transmission/reception aperture 105A is set. On the other hand, when the switches 104A and 104B are in the on state, the signal line group 102 is connected to the three transducer rows 94, 96, and 98. In that case, a large aperture size D2 is set in the y direction. For example, a transmission/reception aperture 105B is set. The operation of the switches 104A and 104B is controlled by the control unit.

Figure 17:
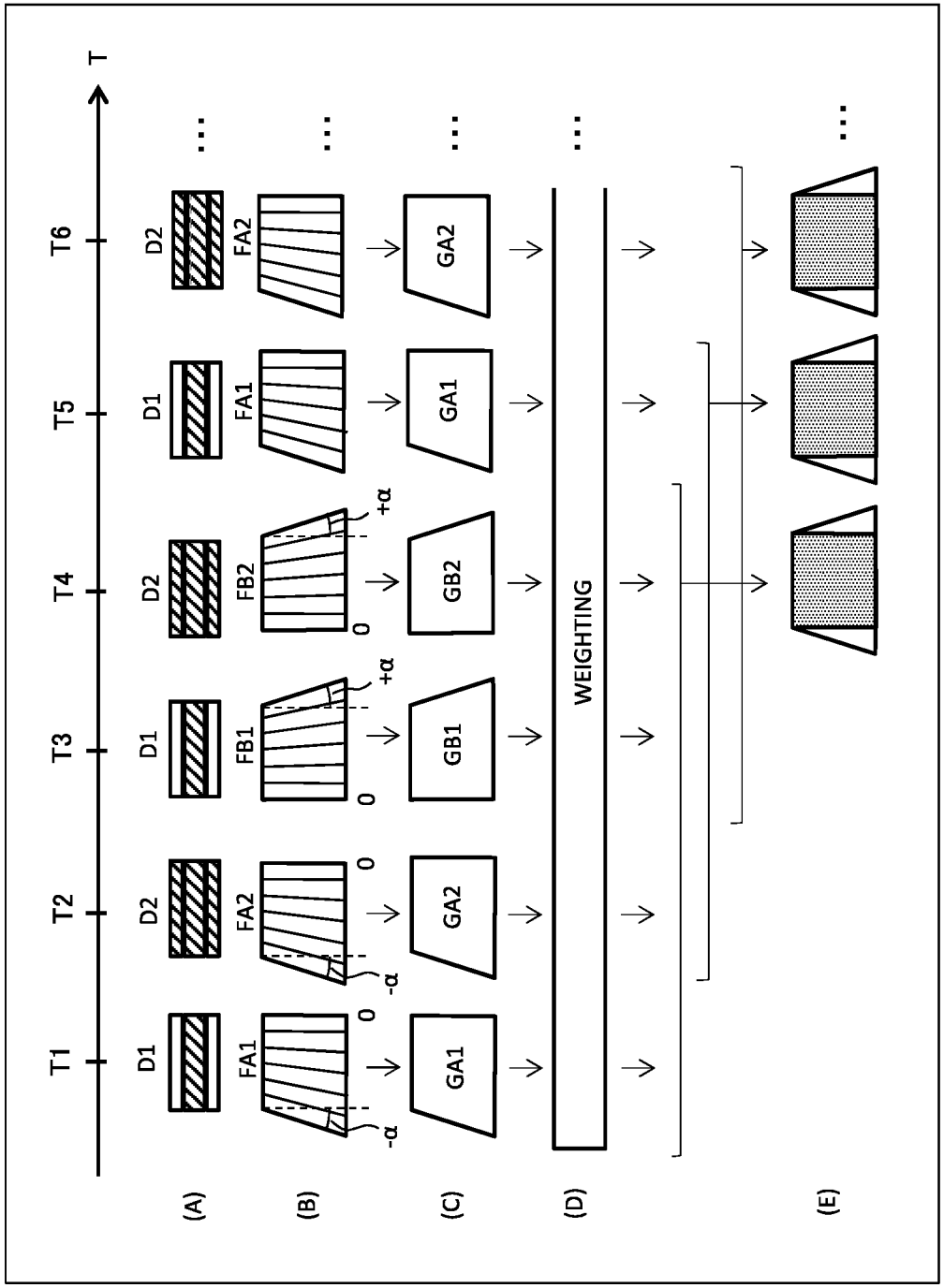
FIG. 17 illustrates a spatial compounding technique according to the third embodiment of the present disclosure.

FIG. 17 illustrates a spatial compounding technique according to the third embodiment of the present disclosure. (A) illustrates switching of aperture sizes in the lateral axis direction. The small aperture size D1 and the large aperture size D2 are set alternately.

The beam scanning plane array illustrated in (B) includes a first beam scanning plane FA1, a second beam scanning plane FA2, a third beam scanning plane FB1, and a fourth beam scanning plane FB2. The first beam scanning plane FA1 is composed of a plurality of first beams formed under the small aperture size D1. The beam deflection angle of the plurality of first beams increases continuously from the first end to the second end in the electronic scanning direction toward the negative side from 0 degrees to −α degrees.

The second beam scanning plane FA2 is composed of a plurality of second beams formed under the large aperture size D2. The beam deflection angle of the plurality of second beams increases continuously from the first end to the second end in the electronic scanning direction toward the negative side from 0 degrees to −α degrees.

The third beam scanning plane FB1 is composed of a plurality of third beams formed under the small aperture size D1. The beam deflection angle of the plurality of third beams increases continuously from the second end to the first end in the electronic scanning direction toward the positive side from 0 degrees to +α degrees.

The fourth beam scanning plane FB2 is composed of a plurality of fourth beams formed under the large aperture size D2. The beam deflection angle of the plurality of fourth beams increases continuously from the second end to the first end in the electronic scanning direction toward the positive side from 0 degrees to +α degrees.

The frame array illustrated in (C) includes a first frame GA1 obtained from the first beam scanning plane FA1, a first frame GA2 obtained from the second beam scanning plane FA2, a first frame GB1 obtained from the third beam scanning plane FB1, and a first frame GB2 obtained from the fourth beam scanning plane FB2. (D) illustrates weighted synthesis that is applied to four temporally successive frames.

Figure 18:
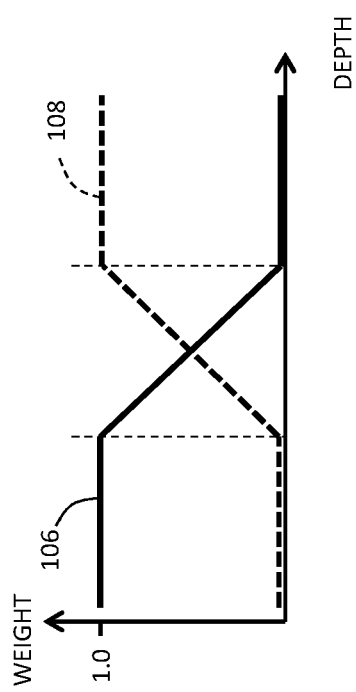
FIG. 18 illustrates a weighting function.

For example, weighting functions 106 and 108 illustrated in FIG. 18 are used. The horizontal axis represents depth (or propagation distance), and the vertical axis represents weight. The weighting function 106 is applied when the small aperture size D1 is set, and the weighting function 108 is applied when the large aperture size D2 is set.

After the respective frames are subjected to their corresponding weighting functions, four weighted frames are synthesized. The weighted synthesis is performed on each set of four frames that are successive on the time axis, thereby generating a synthesized frame array illustrated in (E).

The fourth embodiment provides good spatial compounding effect anywhere from shallow to deep points. That is, the image quality of ultrasound images is improved. The first beam scanning plane FA1, the second beam scanning plane FA2, the third beam scanning plane FB1, and the fourth beam scanning plane FB2 may be formed in any predetermined order.

Figure 19:
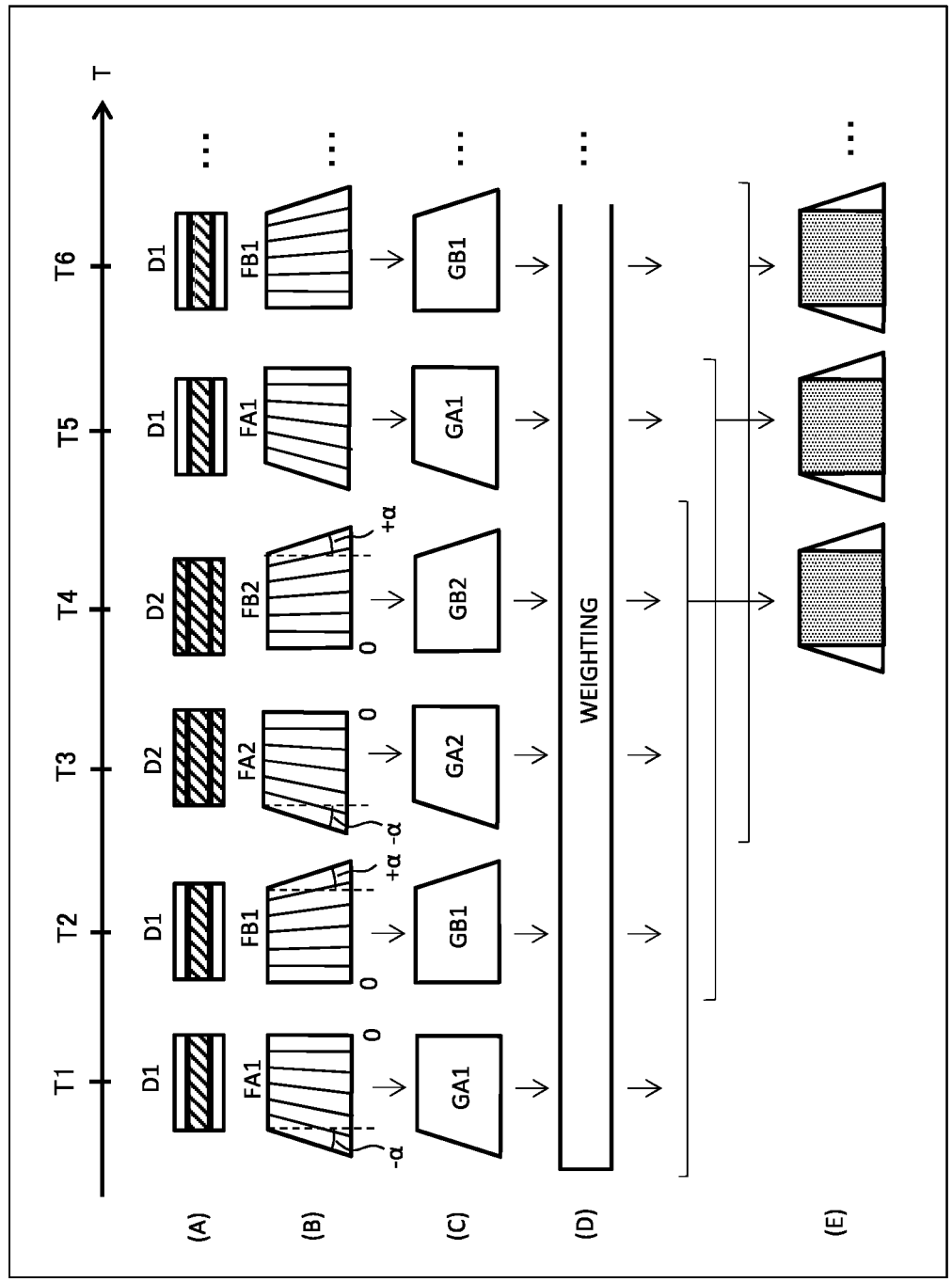
FIG. 19 illustrates a modification of the third embodiment of the present disclosure.

For example, as illustrated in FIG. 19, a plurality of beam scanning planes may be formed cyclically in the following order: the first beam scanning plane FA1, the third beam scanning plane FB1, the second beam scanning plane FA2, and the fourth beam scanning plane FB2.

Figure 20:
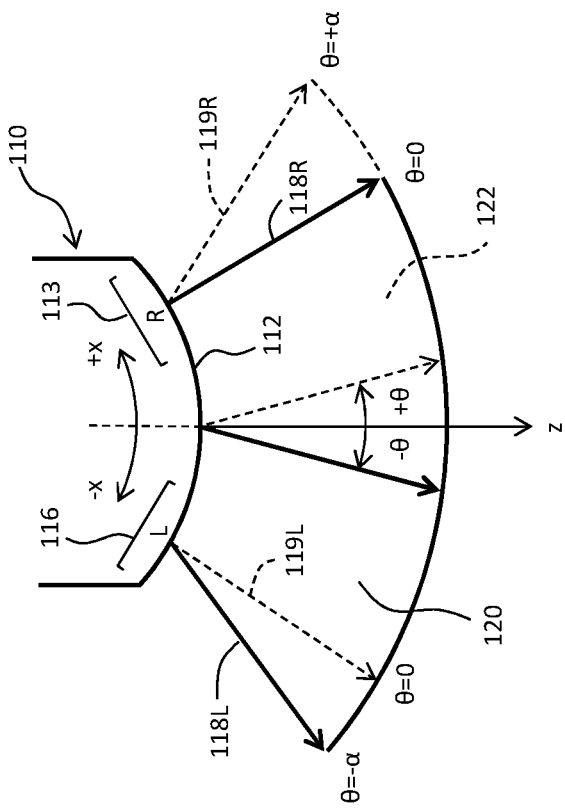
FIG. 20 illustrates convex scanning.

As illustrated in FIG. 20, a spatial compounding technique according to an embodiment of the present disclosure may be applied to a convex probe. Referring to FIG. 20, a convex probe 110 includes a transducer array 112 consisting of a plurality of transducers that are aligned in an arc arrangement. The negative electronic scanning direction is denoted as −x, and the positive electronic scanning direction is denoted as +x. R represents the first end in the electronic scanning direction, and L represents the second end in the electronic scanning direction. Reference numeral 113 represents a transmission/reception aperture that is set with the first end R at the center, and reference numeral 116 represents a transmission/reception aperture that is set with the second end L at the center. z represents depth direction. As already described, the transmission/reception aperture may be set to either extend partially beyond the transducer array 112 or extend across an actual end of the transducer array 112.

A first beam scanning plane 120 and a second beam scanning plane 122 are formed alternately. The first beam scanning plane 120 is composed of a plurality of first beams. The plurality of first beams are composed of n first beams including a first beam 118R corresponding to the first end R to a first beam 118L corresponding to the second end L. The beam deflection angle θ of the first beam 118R is 0 degrees, and the beam deflection angle θ of the first beam 118L is −α. The beam deflection angle θ increases continuously toward the negative side (−θ side) from the first end R to the second end L in the electronic scanning direction.

The second beam scanning plane 122 is composed of a plurality of second beams. The plurality of second beams are composed of n second beams including a second beam 119L corresponding to the second end L to a second beam 119R corresponding to the first end R. The beam deflection angle θ of the second beam 119L is 0 degrees, and the beam deflection angle θ of the second beam 119R is +α. The beam deflection angle θ increases continuously toward the positive side (+θ side) from the second end L to the first end R in the electronic scanning direction. As described above, a spatial compounding technique according to an embodiment of the present disclosure may also be applied to a convex probe.

The invention claimed is:
1. An ultrasound diagnostic apparatus comprising:
a transducer array including a plurality of transducers that are successive in an electronic scanning direction;
a controller that controls operation of the transducer array to successively form a plurality of beam scanning planes including a first beam scanning plane and a second beam scanning plane; and a synthesizer that synthesizes a plurality of items of frame data that are obtained through formation of the plurality of beam scanning planes, wherein the first beam scanning plane is composed of a plurality of first beams that are successive in the electronic scanning direction, and a deflection angle of the plurality of first beams increases continuously toward a negative side from a first end to a second end in the electronic scanning direction, wherein a beam deflection angle difference between adjacent first beams on the first beam scanning plane increases gradually from the first end to the second end in the electronic scanning direction, wherein the second beam scanning plane is composed of a plurality of second beams that are successive in the electronic scanning direction, and a deflection angle of the plurality of second beams increases continuously toward a positive side from the second end to the first end, and wherein a beam deflection angle difference between adjacent second beams on the second beam scanning plane increases gradually from the second end to the first end in the electronic scanning direction.

2. The ultrasound diagnostic apparatus according to claim 1, wherein the controller sets the deflection angle of the plurality of first beams according to a first beam deflection angle function, and sets the deflection angle of the plurality of second beams according to a second beam deflection angle function, wherein in a coordinate system defined by a first axis that represents position of a transducer in the transducer array and a second axis that represents beam deflection angle, the first beam deflection angle function is represented by a first line, and the second beam deflection angle function is represented by a second line, and wherein in the coordinate system, each of the first line and the second line is either a straight line or a curve.

3. The ultrasound diagnostic apparatus according to claim 2, wherein in the coordinate system, the first line and the second line are parallel with each other.

4. The ultrasound diagnostic apparatus according to claim 3, wherein in the coordinate system, each of the first line and the second line is a straight line.

5. The ultrasound diagnostic apparatus according to claim 1, wherein on the first beam scanning plane, the deflection angle of a first beam corresponding to the first end is 0 degrees or $+\zeta$ degrees, and the deflection angle of a first beam corresponding to the second end is $-\alpha$ degrees (where $|\alpha|>0$ or $|\alpha|>|\zeta|>0$), and wherein on the second beam scanning plane, the deflection angle of a second beam corresponding to the second end is 0 degrees or $-\zeta$ degrees, and the deflection angle of a second beam corresponding to the first end is $+\alpha$ degrees.

6. The ultrasound diagnostic apparatus according to claim 1, wherein the transducer array includes a plurality of transducer rows that are successive in a lateral axis direction that is perpendicular to a longitudinal axis direction serving as the electronic scanning direction, wherein each of the transducer rows is composed of a plurality of transducers that are successive in the electronic scanning direction, wherein the plurality of beam scanning planes include the first beam scanning plane, the second beam scanning plane, a third beam scanning plane, and a fourth beam scanning plane, wherein the third beam scanning plane is composed of a plurality of third beams that are successive in the electronic scanning direction, wherein the deflection angle of the plurality of third beams increases continuously toward the negative side from the first end to the second end, wherein the fourth beam scanning plane is composed of a plurality of fourth beams that are successive in the electronic scanning direction, wherein the deflection angle of the plurality of fourth beams increases continuously toward the positive side from the second end to the first end, wherein to form the first beam scanning plane and the second beam scanning plane, a first aperture size is set in the lateral axis direction in the transducer array, wherein to form the third beam scanning plane and the fourth beam scanning plane, a second aperture size is set in the lateral axis direction in the transducer array, and wherein the first aperture size and the second aperture size are different from each other.

7. The ultrasound diagnostic apparatus according to claim 1, comprising a filter that works on a plurality of first reception signals corresponding to the plurality of first beams and a plurality of second reception signals corresponding to the plurality of second beams, wherein the controller varies characteristics of the filter in accordance with the deflection angle of the plurality of first beams and the deflection angle of the plurality of second beams.

8. The ultrasound diagnostic apparatus according to claim 1, wherein a count of the plurality of beam scanning planes is an even number, and wherein a beam scanning plane set consisting of the even number of beam scanning planes is formed cyclically.

* * * * *